United States Patent
Okano et al.

(10) Patent No.: US 7,662,385 B2
(45) Date of Patent: Feb. 16, 2010

(54) AGENT FOR INHIBITING PROLIFERATION OF NEURAL STEM CELLS

(75) Inventors: Hideyuki Okano, Tokyo (JP);
Kazunobu Sawamoto, Tokyo (JP);
Masanori Sakaguchi, Toronto (CA);
Jun Hirabayashi, Ibaraki (JP)

(73) Assignees: Keio University, Tokyo (JP); Advanced Industrial Science and Technology, Tokyo (JP)

( * ) Notice: Subject to any disclaimer, the term of this patent is extended or adjusted under 35 U.S.C. 154(b) by 0 days.

(21) Appl. No.: 11/704,185

(22) Filed: Feb. 9, 2007

(65) Prior Publication Data

US 2007/0248592 A1    Oct. 25, 2007

(30) Foreign Application Priority Data

Feb. 10, 2006    (JP)    ............................. 2006-034444

(51) Int. Cl.
*C12N 5/00* (2006.01)
*C12N 5/06* (2006.01)
*A61K 39/00* (2006.01)
*A61K 39/395* (2006.01)

(52) U.S. Cl. .................... 424/158.1; 435/368; 435/377; 424/130.1; 530/387.1

(58) Field of Classification Search ........................ None
See application file for complete search history.

(56) References Cited

U.S. PATENT DOCUMENTS

2007/0098701 A1* 5/2007 Okano et al. ............. 424/93.21

FOREIGN PATENT DOCUMENTS

EP         1674566 A1 *  6/2006
WO    WO 2005/026343 A1 *  3/2005

OTHER PUBLICATIONS

Sakaguchi et al., PNAS, USA, 103(18): 7112-7117, published Apr. 24, 2006.*
Moiseeva et al., Biochemical and Biophysical Research Communications, 310:1010-1016, published Sep. 25, 2003.*
Kami et al., Current Drug Targets, 6(4):395-405, Jun. 2005.*
Akiyama, Y. et al., "Transportation of Clonal Neural Precursor Cells Derived from Adult Human Brain Establishes Functional Peripheral Myelin in the Rat Spinal Cord" *Exp. Neurol.* 167:27-39 (2001).

Araujo, D. et al., "Glial Cell Line-derived Neurotrophic Factor Attenuates the Excitotoxin-induced Behavioral and Neurochemical Deficits in a Rodent Model of Huntington's Disease" *Neurosci.* 81:1099-110 (1997).
Bai, H. et al., "Dissemination and Proliferation of Neural Stem Cells on the Spinal Cord by Injection into the Fourth Ventricle of the Rat: A Method for Cell Transplantation" *J. Neurosci. Meth.* 124:181-87(2003).
Bajocchi, G. et al., "Direct in vivo Gene Transfer to Ependymal Cells in the Central Nervous System Using Recombinant Adenovirus Vectors" *Nature Genetics* 3:229-34 (1993).
Fricker, R. et al., "Site-specific Migration and Neuronal Differentiation of Human Neural Progenitor Cells After Transplantation in the Adult Rat Brain" *J. Neurosci.* 19:5990-6005 (1999).
Fuchs, E. et al., "Stem Cells: A New Lease on Life" *Cell* 100:143-55 (2000).
Gage, F. et al., "Survival and Differentiation of Adult Neuronal Progenitor Cells Transplanted to the Adult Brain" *PNAS-USA* 92:11879-83 (1995).
Hirabayashi, J. et al., "Effect of Amino Acid Substitution by Site-directed Mutagenesis on the Carbohydrate Recognition and Stability of Human 14-kDa β-Galactoside-binding Lectin" *J. Biol. Chem.* 266:23648-53 (1991).
Seaberg, R.M. et al., "Adult Rodent Neurogenic Regions: The Ventricular Subependyma Contains Neural Stem Cells, But the Dentate Gyrus Contains Restricted Progenitors" *J. Neurosci.* 22:1784-93 (2002).
Singh, S. et al., "Identification of Human Brain Tumor Initiating Cells" *Nature* 432:396-401 (2004).
Van der Kooy, D. et al., "Why Stem Cells?" *Science* 287:1439-41 (2000).
Wu, S. et al., "Migration, Integration, and Differentiation of Hlppocampus-derived Neurosphere Cells After Transplantation into Injured Rat Spinal Cord" *Neurosci. Lett.* 312:173-76 (2001).

* cited by examiner

*Primary Examiner*—John D. Ulm
*Assistant Examiner*—Stacey MacFarlane
(74) *Attorney, Agent, or Firm*—Finnegan, Henderson, Farabow, Garrett & Dunner, LLP

(57) ABSTRACT

The object of the present invention is to provide methods for inhibiting proliferation of neural stem cells, an agent for inhibiting proliferation of neural stem cells, and methods for using the same. According to the method of the present invention, a galectin-1 inhibitor such as anti-galectin-1 antibody and/or an integrin β1 inhibitor such as anti-integrin β1 antibody is administered to a human or a vertebrate other than human for inhibiting proliferation of neural stem cells. This method can be used for treatment of nerve injury and nerve tumors.

1 Claim, 2 Drawing Sheets

AGENT FOR INHIBITING PROLIFERATION OF NEURAL STEM CELLS

CROSS REFERENCE TO RELATED APPLICATIONS

This application claims the benefit of priority to Japan Patent Application No. 2006-34444, filed on Feb. 10, 2006, which is incorporated herein by reference.

TECHNICAL FIELD

The present invention relates to an agent for inhibiting proliferation of neural stem cells and methods for inhibiting proliferation of neural stem cells.

DESCRIPTION OF THE RELATED ART

To date, transplantation of neural stem cells has been attempted for central nervous system injury (e.g., Van-der-Kooy and Weiss, Science 287:1439-1441 (2000); Fuchsand Segre, Cell 100:143-55 (2000); and Seaberg and van-der-Kooy J Neurosci. 22:1784-1793 (2002)). Approaches have been made also to directly administer stem cells locally, including infusion into the injured brain (e.g., Gage et al., Proc Natl Acad Sci USA 92:11879-11883 (1995); and Fricker et al., J Neurosci. 19:5990-6005 (1999)), infusion into the spinal cord (Akiyama et al. and Exp Neurol. 167:27-39-(2001)), regardless of the presence or absence of artificial substrates such as cell carriers (e.g., Wu et al., Neurosci Lett. 312:173-176 (2001)).

Meanwhile, gene therapeutic agents (e.g., Bajocchi et al. and Nat Genet. 3:229-234 (1993)), neurotrophic factors (e.g., Araujo and Hilt Neuroscience 81:1099-110 (1997)), and agents such as nitecapone have been administered via cerebrospinal fluid (CSF). Based on this approach, neural stem cells were also infused into cerebrospinal fluid. It was shown that when neural stem cells were infused into the cerebrospinal fluid in the fourth ventricle of rats, the cells themselves participate in restoration by recognizing a lesion and migrating into the lesion (e.g., Bai et al. J Neurosci Methods 124: 181-187 (2003)).

However, it was found that proliferation of transplanted neural stem cells will not stop for more than one year; thus developing a method for stopping neural stem cell proliferation for the purpose of clinical application is needed. Thus, the object of the present invention is to provide methods for inhibiting proliferation of neural stem cells, an agent for inhibiting proliferation of neural stem cells, and methods of using the same.

SUMMARY OF THE INVENTION

The inventors have already found that galectin-1 is one of the factors responsible for neural stem cell proliferation, and thus have conducted identification of galectin-1 receptors.

As shown in the Reference Example, adhesion of galectin-1 to neural stem cells was inhibited by lactose (FIG. 1A). In addition, when a column to which galectin-1 had been bound was bound with an extract of SVZ cells, cells present in the subventricular zone, and then eluted with lactose, integrin $\beta 1$ was eluted (FIG. 1B). This demonstrated that the receptor for galectin-1 is integrin $\beta 1$, which is expressed by SVZ cells. As a matter of fact, the region where galectin-1 is expressed and the region where integrin $\beta 1$ is expressed are overlapped on the SVZ (FIG. 1C), supporting that the galectin-1 receptor is integrin $\beta 1$.

Thus, as a result of such diligent study, the inventors of the present application found that the galectin-1 receptor is integrin $\beta 1$. Accordingly, when signals transmitted by galectin-1 to integrin $\beta 1$ was inhibited by infusing anti-integrin $\beta 1$ antibody into the brain, it was found that proliferation of SVZ nerve cells is inhibited, and thus the present invention has been accomplished.

The agent for inhibiting proliferation of neural stem cells according to the present invention contains a binding-inhibiting composition which inhibits the binding between galectin-1 and integrin $\beta 1$. Further, in the method for inhibiting proliferation of neural stem cells according to the present invention, the binding between galectin-1 and integrin $\beta 1$ is inhibited.

The therapeutic agent for nerve injury according to the present invention contains neural stem cells and the above-described agent for inhibiting proliferation. The therapeutic agent for nerve injury is preferably administered to cerebrospinal fluid. Further, in the method for treating nerve injury according to the present invention, neural stem cells and the above-described agent for inhibiting proliferation are administered, preferably to cerebrospinal fluid.

The anti-nerve tumor agent according to the present invention contains a binding-inhibiting composition which inhibits the binding between galectin-1 and integrin $\beta 1$. Further, in the method for treating nerve tumors according to the present invention, the binding between galectin-1 and integrin $\beta 1$ is inhibited.

The binding-inhibiting composition used herein is preferably either anti-galectin-1 antibody or anti-integrin $\beta 1$ antibody.

According to the present invention, methods for inhibiting proliferation of neural stem cells, an agent for inhibiting proliferation of neural stem cells, and methods for using the same can be provided.

DETAILED DESCRIPTION OF THE INVENTION

==Binding-inhibiting Composition==

Figure 1:
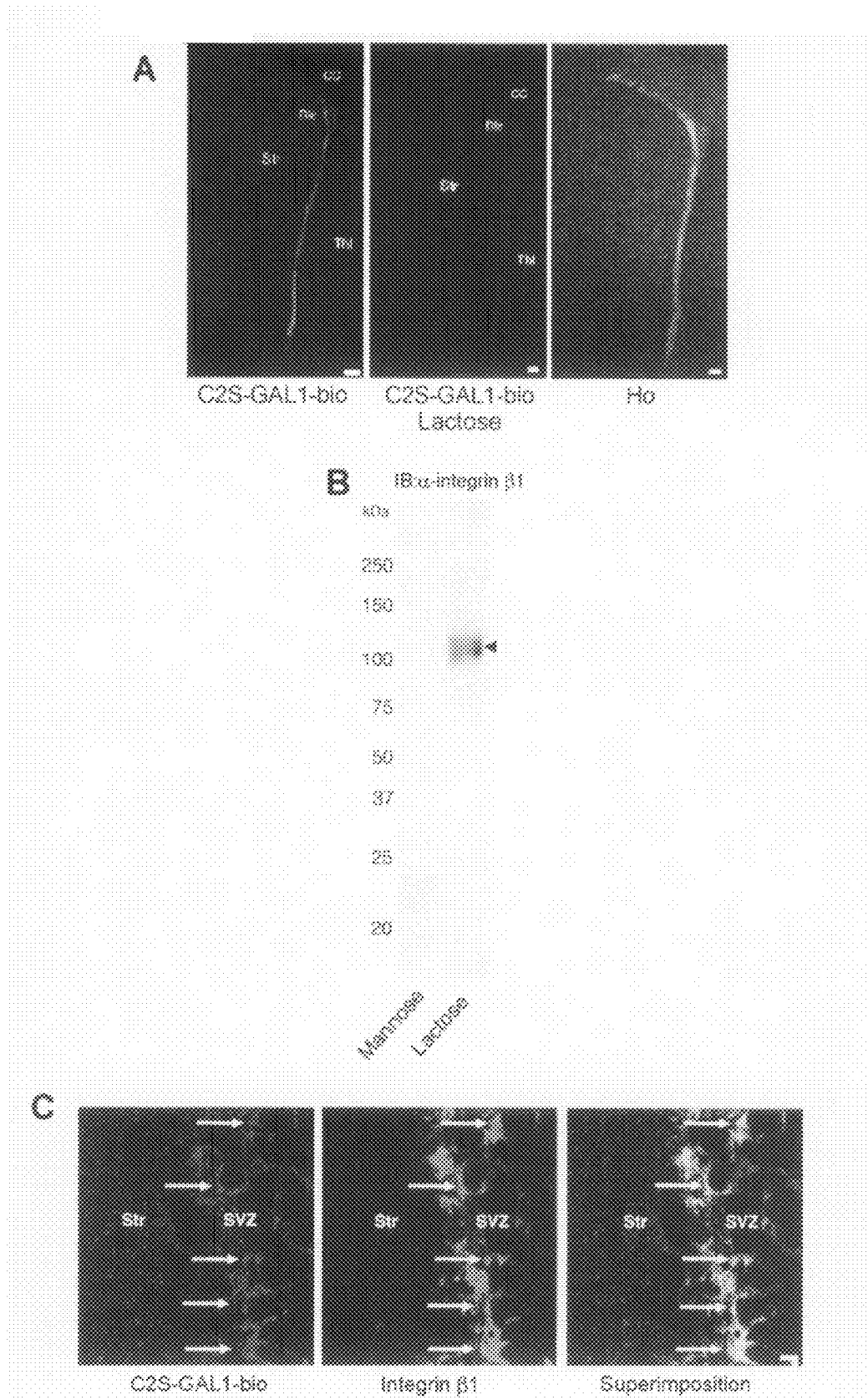
FIG. 1 shows examples of experiments demonstrating that integrin $\beta 1$ is the receptor for galectin-1. (A) is an example of experiment showing that the binding of galectin-1 to neural stem cells is inhibited by lactose in vivo. (B) is an example of experiment showing that integrin $\beta 1$ is bound to a CS-GAL-1 affinity column and then eluted. (C) is an example of experiment showing that cells expressing integrin $\beta 1$ have affinity to galectin-1.

As shown in the experiment of the Reference Example, when galectin-1 enhances neural stem cell proliferation, it transmits its signals to neural stem cells by using integrin $\beta 1$ as the receptor. Therefore, by administering a binding-inhibiting composition which inhibits the binding between galectin-1 and integrin β1, such as anti-integrin β1 antibody having inhibitory activity on the binding of galectin-1, the proliferation signals from galectin-1 to neural stem cells are blocked, and thus neural stem cell proliferation is inhibited.

The binding-inhibiting composition that can be used as above is not limited as long as it is a composition which inhibits the binding between galectin-1 and integrin β1. Besides the above-mentioned anti-integrin β1 antibody, examples of this composition include, but are not limited to, anti-galectin-1 antibody, a RGD peptide, laminin, fibronectin, etc., which have inhibitory activity on integrin β1.

==Method for Administering a Binding-inhibiting Composition==

As described above, by reacting a binding-inhibiting composition which inhibits the binding between galectin-1 and integrin β1 with neural stem cells, proliferation of the neural stem cells can be inhibited.

The method for administering the binding-inhibiting composition is not particularly limited. When neural stem cell proliferation within the brain is to be inhibited, the binding-inhibiting composition may be locally infused into, for example, a lateral ventricle or an injured brain tissue, or may be delivered to the desired site by being infused into cerebrospinal fluid (CSF) or blood. Specifically, methods such as one that uses an osmotic pump for administration of a binding-inhibiting composition are known (refer to the Journal of the Physiological Society of Japan, Vol. 63 No. 10 pp. 261-270 for more detail).

==Application to Nerve Injury Treatment==

As described above, it has been shown that when neural stem cells are infused into the cerebrospinal fluid in the fourth ventricle of rats, the cells themselves participate in restoration by recognizing a lesion and migrating into the lesion (e.g., Bai et al., J Neurosci Methods 124:181-187 (2003)). However, proliferation of transplanted neural stem cells would not stop for more than one year. In such a case, the proliferation of the neural stem cells can be inhibited by administering a binding-inhibiting composition which inhibits binding between galectin-1 and integrin β1, according to the present invention.

For example, in humans or vertebrates other than humans afflicted with nerve injury, neural stem cells are allowed to proliferate in injured site by infusing neural stem cells into cerebrospinal fluid (CSF). After the neural stem cells have proliferated to a suitable degree, their proliferation can then be inhibited by infusing a binding-inhibiting composition which inhibits the binding between galectin-1 and integrin β1 into the cerebrospinal fluid (CSF). The timing of administration of the binding-inhibiting composition can be determined depending on the purpose: the composition may be administered concomitantly with the neural stem cells or may be administered at a time remote from the administration of the neural stem cells. The mode of administration of the neural stem cells or the binding-inhibiting composition is not particularly limited; they may be infused locally or into the cerebrospinal fluid, either to the same site or to different sites.

==Application to Tumor Therapy==

A malignant tumor is a pathological condition in which (1) cells having lost their normal differentiating ability (2) acquire self-replicating ability and proliferate abnormally, thereby destroying normal cells.

It has been shown that, in leukemia, a small number of tumor stem cells are the origin of cells in tumor tissue and maintain the tumor tissue as a cellular mass. The same hypothesis has been raised for solid tumors. However, the presence of tumor stem cells was not known except for breast tumor. Sheila et al. recently discovered that CD133-positive cells have the characteristics of tumor stem cells (Sheila K. Singh et al., Nature 432, 396-401-(2004)), demonstrating the presence of tumor stem cells in brain tumors as well. There are many commonalities as stem cells between the neural tumor stem cell and the neural stem cell in that, e.g. the CD133 marker is originally a neural stem cell marker. It is also suggested that normal stem cells can transform into tumor stem cell; if neural stem cell proliferation can be inhibited, proliferation of neural tumor stem cells would probably be inhibited as well. Further, considering the fact that simultaneous activation of Ras and Akt in neural progenitors results in glioblastoma and the like, if proliferation of neural tumor stem cells can be inhibited, growth of neural tumors could be inhibited as well. Therefore, the binding-inhibiting composition having the effect of inhibiting neural stem cell proliferation is useful as an anti-neural tumor agent.

As used herein, a "neural tumor" refers to a tumor consisting of tumor cells which have developed from neural cells. Neural tumors include, but are not limited to, neuroblastoma, glioblastoma, etc.

EXAMPLES

Reference Example

==Demonstration that Integrin β1 is the Receptor of Galectin-1==

To examine whether glucose is involved in the binding of galectin-1 to neural stem cells, tissue staining was performed with biotinylated C2S galectin-1 (C2S-GAL-1-bio) in the presence of lactose (provided by the National Institute of Advanced Industrial Science and Technology). This C2S-GAL-1, a galectin-1 mutant in which cysteine at position 2 is replaced with serine (Hirabayashi & Kasai, J Biol. Chem. 266, 23648-23653, 1991), has been found to have normal carbohydrate binding ability (Purkrabkova et al. Biol. Cell. 95, 535-545, 2003).

First, the brain was removed from 56-day to 105-day old mice, perfusion-fixed with 4% formaldehyde solution, post-fixed at 4° C. overnight in the same solution, and 50 μm thick vibratome sections were prepared.

These sections were incubated at 4° C. overnight in a 1 μg/mL C2S-GAL-1-bio solution dissolved in PBS containing 0.5% Triton X-100 and 1% BSA in the presence of 20 mM lactose. Fluorescent staining was performed by using the Vectastain ABC kit (Vector Laboratories) and TSA (PerkinElmer, Inc.). As a result, the signals became significantly weak, as compared with the control, which did not contain lactose, (FIG. 1A). This indicates that the binding of galectin-1 to neural stem cells is inhibited by lactose.

To explore the mechanism of this inhibition of binding by lactose and to identify the galectin-1 binding factor, the galectin-1 binding factor was isolated from an extract of SVZ by using a C2S-GAL-1 affinity column. First, recombinant C2S-GAL-1 was immobilized on an NHS-activated Sepharose column (Amersham), packed in a 2 ml volume column, and equilibrated with PBS containing 2 mM EDTA and 4 mM 2-mercaptoethanol (ME-PBS). Meanwhile, brains were removed from five adult mice, and SVZ tissues were excised with an ophthalmic scalpel under a stereoscopic microscope. The SVZ tissues obtained after sonication were subjected to three times of washing by pipetting in ME-PBS containing 20 mM lactose (Wako) and centrifugation and removal of the supernatant, and finally solubilized with ME-PBS containing 1% Triton X-100, and was injected onto the column being equilibrated with ME-PBS. After nonspecifically bound molecules were removed by washing the column with ME-PBS containing 100 mM α-methylmannopyranoside (Sigma), elution was performed with ME-PBS containing 20 mM lactose or 100 mM mannose (Wako). Western blotting was performed to examine whether integrin β1 was present in the effluent. Integrin β1 was detected by using anti-integrin antibody (mouse anti-integrin B1, IgG monoclonal, BD, 1:100 dilution) as the primary antibody) and HRP labeled anti-mouse IgG (Jackson Immunoresearch Labs, 1:500 dilution) as the secondary antibody. As the result indicated, whereas with lactose-containing ME-PBS, integrin β1 was eluted, with mannose-containing ME-PBS, integrin β1 was not eluted (FIG. 1B). Considering that lactose inhibits the binding of galectin-1 to its receptor, at least, integrin β1 was inferred to be the galectin-1 receptor on neural stem cells. Thus, double staining was performed on the previously-described vibratome sections of mouse brain by using C2S-GAL-1 and the anti-integrin antibody (Pharmingen, 1:10 dilution). For the detection of C2S-GAL-1, the Vectastain ABC kit (Vector Laboratories) and TSA (PerkinElmer, Inc.) were used. For the detection of integrin, anti-mouse IgG antibody (Jackson, 1:500 dilution) was used as the secondary antibody. As shown in FIG. 1C, cells in which integrin β1 was expressed had affinity to C2S-GAL-1, supporting that the receptor for galectin-1 is integrin β1.

Example

It is known that, in the SVZ, some of SVZ astrocytes function as neural stem cells and differentiate via amplifying cells (TA cells) at an intermediate stage of differentiation and further proliferation, into neuroblasts (NBs). These neural stem cells are known to proliferate comparatively slowly and thus can be identified by allowing them to incorporate BrdU for a long period.

Meanwhile, infusion of galectin into the mouse brain enhances proliferation of the neural stem cells in the SVZ (REF). Thus, the effect of inhibition of the interaction between galectin-1 and integrin β1 on proliferation of the neural stem cells was examined.

First, recombinant galectin-1 (2 or 14 μg), an anti-galectin neutralizing antibody (rabbit IgG, 30 μg/ml, provided by Kirin Brewery), a control antibody which does not recognize galectin (rabbit IgG, 30 μg/ml, provided by Kirin Brewery), an anti-integrin β1 antibody (hamster IgM, 10 μg/ml, BD), and a control antibody which does not recognize integrin β1 (hamster IgM, 10 μg/ml, BD) were dissolved each in 0.9% saline containing 1 mg/ml mouse serum albumin (Sigma). Using stereotaxic surgery, a cannula was inserted and placed at a position 0.2 mm posterior and 0.8 mm lateral to the bregma, and 2.0 mm deep from the skull surface, and the galectin solution was continuously infused into the lateral ventricle at a rate of 0.5 μl/h with an osmotic pump for 7 days (FIG. 2A).

To examine proliferation of neural stem cells in the above-described conditions, the proliferating cells were visualized by allowing BrdU to be incorporated in the cells for a long period. First, mice received water containing 1 mg/ml BrdU as drinking water (FIG. 2A) throughout the 7-day continuous administration of galectin-1 (FIG. 2B and C), or throughout the 7-day continuous administration of galectin-1 plus anti-integrin antibody (FIG. 3A and B). Either 17 and 37 days (FIG. 2B and C) or 17 days (FIG. 3A and B) after the last day of the administrations, the mice were dissected and the brains were removed. Vibratome sections were prepared from the SVZ region as described above. Using a rat anti-BrdU monoclonal antibody (rat monoclonal antibody [BU 1/75 (ICR)], 1:100 dilution, Abcam, Inc.) as the primary antibody and a biotin-labeled anti-rat IgG antibody (1:100 dilution, Jackson ImmunoResearch Labs) as the secondary antibody, the sections were observed with a confocal laser microscope (LSM-510, Zeiss) (FIGS. 2B and 3A). In addition, to quantify signals, a 1 μm thick cross section was taken at every 7 μm in the SVZ region (bregma+0 to +1) and the number of BrdU-positive nuclei was counted. The results were plotted (FIGS. 2C and 3B).

Figure 2:
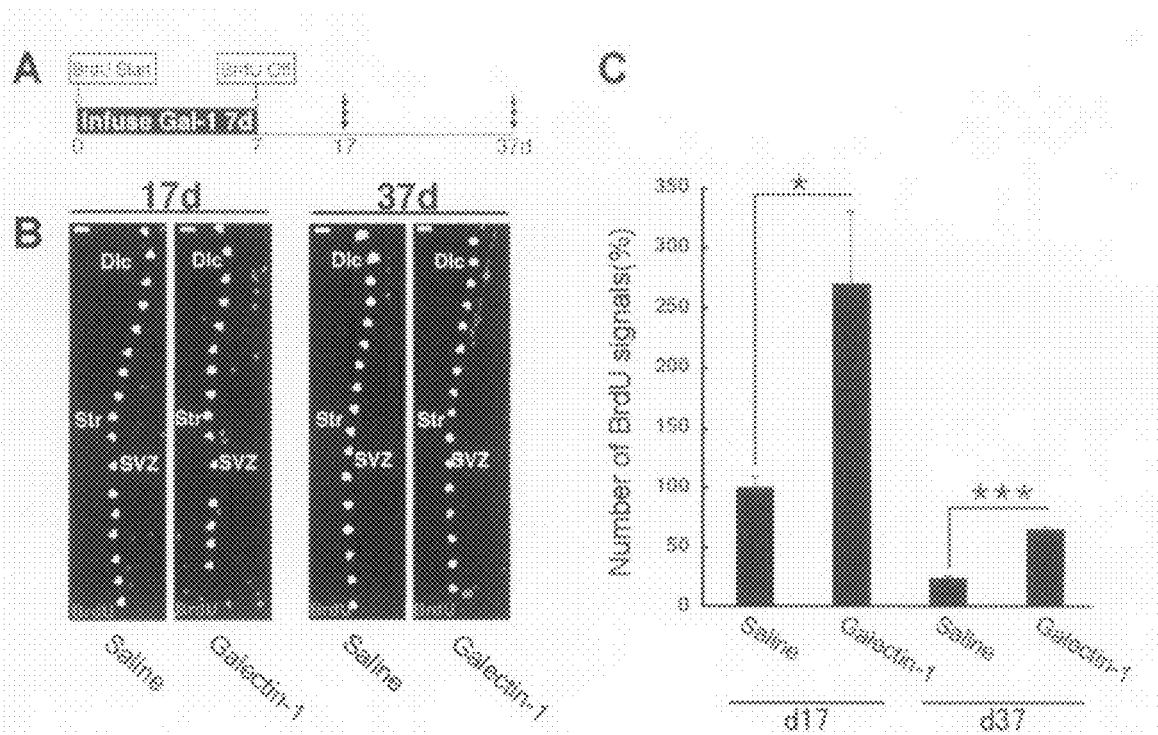
FIG. 2 shows a result obtained by allowing BrdU to be incorporated in neural stem cells simultaneously when galectin-1 was infused into a brain in the Examplet. (A) shows the method for administering BrdU and galectin-1 in the Example. (B) shows a result of in situ visualization of proliferating cells. (C) shows a result of counting the number of BrdU-positive nuclei.
Figure 3:
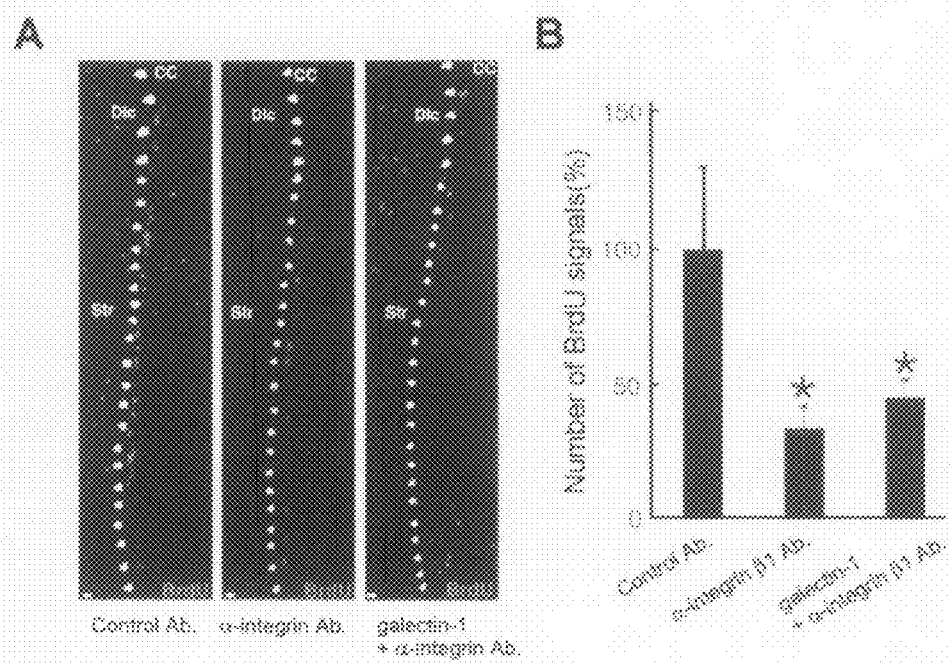
FIG. 3 shows a result obtained by allowing BrdU to be incorporated into a brain at the same time when galectin-1 and anti-integrin antibody were infused into the brain in the Example. (A) shows a result of in situ visualization of proliferating cells. (B) shows a result of counting the number of BrdU-positive nuclei.

As shown in FIG. 2B and C, in the mouse receiving galectin, the number of slowly proliferating cells in the SVZ was significantly increased as compared with untreated control mice both on day 37 and on day 17 (on day 17 p=0.01; on day 37 p<0.001). This result indicated that infusion of galectin-1 into the brain increases the number of neural stem cells.

Meanwhile, as shown in FIG. 3A and B, in the mice receiving the anti-integrin antibody, the number of slowly proliferating cells was significantly decreased in the SVZ, as compared with the untreated control mice (p<0.05). This result indicated that infusion of the anti-integrin antibody into the brain decreases the number of neural stem cells.

Moreover, although galectin-1 was administered, the effect of galectin-1 was not exerted and the number of slowly proliferating cells was significantly decreased (p<0.05) when the anti-integrin antibody was concomitantly administered. This result indicated that the decrease in the number of neural stem cells due to anti-integrin antibody was caused by the inhibition of the interaction between galectin-1 and integrin by the anti-integrin antibody.

These results clarified that, by inhibiting the interaction between galectin-1 and integrin, proliferation of neural stem cells can be inhibited.

What is claimed is:

1. A method for inhibiting proliferation of a neural stem cell, comprising administering an anti-galectin-1 antibody, wherein the antibody inhibits the binding between galectin-1 and integrin β1 on the neural stem cell.

* * * * *